US012668849B2

(12) United States Patent
Jiang et al.

(10) Patent No.: US 12,668,849 B2
(45) Date of Patent: Jun. 30, 2026

(54) METHOD AND KIT FOR MULTIPLE DETECTION OF RESPIRATORY VIRUS NUCLEIC ACIDS

(71) Applicant: Daan Gene Co., Ltd., Guangzhou (CN)

(72) Inventors: Xiwen Jiang, Guangzhou (CN); Taosheng Huang, Guangzhou (CN); Xinyu Li, Guangzhou (CN); Zhiwen Huang, Guangzhou (CN); Weiping Lin, Guangzhou (CN)

(73) Assignee: Daan Gene Co., Ltd., Guangdong (CN)

( * ) Notice: Subject to any disclaimer, the term of this patent is extended or adjusted under 35 U.S.C. 154(b) by 606 days.

(21) Appl. No.: 18/245,822

(22) PCT Filed: Nov. 10, 2020

(86) PCT No.: PCT/CN2020/127755
§ 371 (c)(1),
(2) Date: Mar. 17, 2023

(87) PCT Pub. No.: WO2022/057060
PCT Pub. Date: Mar. 24, 2022

(65) Prior Publication Data
US 2024/0002960 A1     Jan. 4, 2024

(30) Foreign Application Priority Data
Sep. 17, 2020    (CN) .......................... 202010980496.9

(51) Int. Cl.
*C12Q 1/70*         (2006.01)
(52) U.S. Cl.
CPC ......... *C12Q 1/701* (2013.01); *C12Q 2600/16* (2013.01)
(58) Field of Classification Search
CPC ...................................................... C12Q 1/701
See application file for complete search history.

(56) References Cited

FOREIGN PATENT DOCUMENTS

| | | |
|---|---|---|
| CN | 102337352 A | 2/2012 |
| CN | 110273026 A | 9/2019 |
| CN | 110331232 A | 10/2019 |
| CN | 110343784 A | 10/2019 |
| CN | 110408725 A | 11/2019 |
| CN | 111041129 A | 4/2020 |
| CN | 111074011 A | 4/2020 |
| CN | 111088408 A | 5/2020 |
| CN | 111254228 A | 6/2020 |
| CN | 111321251 A | 6/2020 |
| CN | 111349720 A | 6/2020 |
| CN | 111349721 A | 6/2020 |
| CN | 111411172 A | 7/2020 |
| CN | 111440897 A | 7/2020 |
| CN | 111458500 A | 7/2020 |
| CN | 111518960 A | 8/2020 |
| CN | 111593142 A | 8/2020 |
| CN | 111663007 A | 9/2020 |
| CN | 112063756 A | 12/2020 |
| CN | 112342315 B | 3/2022 |

OTHER PUBLICATIONS

Lassauniere, R., et al., 2010, A novel multiplex real-time RT-PCR assay with FRET hybridization probes for the detection and quantitation of 13 respiratory viruses, J. Virol. Meth. 165:254-260.*
International Search Report and Written Opinion (with English translation of ISR) issued in PCT/CN2020/127755, dated Jun. 24, 2021, 18 pages provided.
The extended European search report issued in European Application No. 20953917.0, mailed Oct. 9, 2024.

* cited by examiner

*Primary Examiner* — Jeffrey S Parkin
(74) *Attorney, Agent, or Firm* — HSML P.C.

(57) ABSTRACT
Provided in the present invention are a method and a kit for multiple detection of respiratory virus nucleic acids, and in particular, disclosed are a method, a primer, a probe and a kit for detecting a plurality of influenza A viruses such as H1N1(2019), H3N2, H5N1, H1N1 and H7N9, influenza B viruses such as Yamagata and Victoria, 2019-nCoV OFR1ab and N genes, and human internal standard gene GAPDH on the basis of a real-time fluorescent quantitative PCR technical platform.

7 Claims, 5 Drawing Sheets

Specification includes a Sequence Listing.

SEQUENCE LISTING

<160> NUMBER OF SEQ ID NOS: 21

<210> SEQ ID NO 1
<211> LENGTH: 21
<212> TYPE: DNA
<213> ORGANISM: Artificial sequence
<220> FEATURE:
<223> OTHER INFORMATION: Primer

<400> SEQUENCE: 1
agaccaatcc tgtcacctct g                                          21

<210> SEQ ID NO 2
<211> LENGTH: 19
<212> TYPE: DNA
<213> ORGANISM: Artificial sequence
<220> FEATURE:
<223> OTHER INFORMATION: Primer

<400> SEQUENCE: 2
cgtctacgct gcagtcctc                                             19

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
gcgctactat actgtctcat gg                                         22

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
ttgtttctcg cataaagcac a                                          21

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
caaagaatgc tattagaaaa gtgtg                                      25

<210> SEQ ID NO 6
<211> LENGTH: 21
<212> TYPE: DNA
<213> ORGANISM: Artificial sequence
<220> FEATURE:
<223> OTHER INFORMATION: Primer

<400> SEQUENCE: 6
cgacattcat cattatgcct t                                          21

<210> SEQ ID NO 7
<211> LENGTH: 23
<212> TYPE: DNA
<213> ORGANISM: Artificial sequence -continued

```
<220> FEATURE:
<223> OTHER INFORMATION: Primer

<400> SEQUENCE: 7
accaggaact aatcagacaa gga                                    23

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
ggtgtgactt ccatgccaat                                       20

<210> SEQ ID NO 9
<211> LENGTH: 18
<212> TYPE: DNA
<213> ORGANISM: Artificial sequence
<220> FEATURE:
<223> OTHER INFORMATION: Primer

<400> SEQUENCE: 9
agatttggac ctgcgagc                                         18

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
actgaatagc caaggtgagc                                       20

<210> SEQ ID NO 11
<211> LENGTH: 21
<212> TYPE: DNA
<213> ORGANISM: Artificial sequence
<220> FEATURE:
<223> OTHER INFORMATION: Probe

<400> SEQUENCE: 11
ttgtattcac gctcaccgtg c                                     21

<210> SEQ ID NO 12
<211> LENGTH: 25
<212> TYPE: DNA
<213> ORGANISM: Artificial sequence
<220> FEATURE:
<223> OTHER INFORMATION: Probe

<400> SEQUENCE: 12
tcctggaaat tattcaatgc aagta                                 25

<210> SEQ ID NO 13
<211> LENGTH: 22
<212> TYPE: DNA
<213> ORGANISM: Artificial sequence
<220> FEATURE:
<223> OTHER INFORMATION: Probe

<400> SEQUENCE: 13
aaattatggt gatagtgcaa ca                                    22
```

<210> SEQ ID NO 14
<211> LENGTH: 20
<212> TYPE: DNA
<213> ORGANISM: Artificial sequence
<220> FEATURE:
<223> OTHER INFORMATION: Probe

<400> SEQUENCE: 14
cacaatttgc ccccagcgct                                                                                        20

<210> SEQ ID NO 15
<211> LENGTH: 20
<212> TYPE: DNA
<213> ORGANISM: Artificial sequence
<220> FEATURE:
<223> OTHER INFORMATION: Probe

<400> SEQUENCE: 15
tccacaagtc cgcgcagagc                                                                                        20

<210> SEQ ID NO 16
<211> LENGTH: 22
<212> TYPE: DNA
<213> ORGANISM: Artificial sequence
<220> FEATURE:
<223> OTHER INFORMATION: Primer

<400> SEQUENCE: 16
cgggtgttgc tatgcctaat ct                                                                                     22

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
ttgcgacatt catcattatg cc                                                                                     22

<210> SEQ ID NO 18
<211> LENGTH: 26
<212> TYPE: DNA
<213> ORGANISM: Artificial sequence
<220> FEATURE:
<223> OTHER INFORMATION: Primer

<400> SEQUENCE: 18
cccaaaatta caatctagtc aagcgt                                                                                 26

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
tgacacagtt gagtatattt tgcgac                                                                                 26

<210> SEQ ID NO 20
<211> LENGTH: 26
<212> TYPE: DNA
<213> ORGANISM: Artificial sequence
<220> FEATURE:
<223> OTHER INFORMATION: Primer -continued

```
<400> SEQUENCE: 20
ggccatgtag aaacatttta cccaaa                                                    26

<210> SEQ ID NO 21
<211> LENGTH: 26
<212> TYPE: DNA
<213> ORGANISM: Artificial sequence
<220> FEATURE:
<223> OTHER INFORMATION: Primer

<400> SEQUENCE: 21
ttgagtatat tttgcgacat tcatca                                                    26
```

METHOD AND KIT FOR MULTIPLE DETECTION OF RESPIRATORY VIRUS NUCLEIC ACIDS

TECHNICAL FIELD

The present invention relates to the field of biotechnology. Specifically, the invention relates to a method, a primer, a probe and a kit comprising the primer-probe mixture for qualitatively detecting influenza A virus, influenza B virus and 2019-nCoV nucleic acid in samples such as human nasopharyngeal swabs, throat swabs, and sputum based on a real-time fluorescent quantitative PCR detection technology platform.

BACKGROUND

Type A influenza is a disease syndrome co-affected by human and animals caused by Influenza A. After poultry are infected with Influenza A, there may be subclinical symptoms to mild upper respiratory symptoms, fatigue, and even systemic fatal disease syndrome. At present, many influenza A viruses such as H1N1, H3N2, H5N1, H9N2, H7N9, etc. have been transmitted from birds to humans, and the mortality rate is extremely high, leading to serious public health incidents. The clinical symptoms of different strains of infection are highly similar and difficult to distinguish from other pathogens that cause influenza-like symptoms. Surveillance is the basis for determining the circulating strains of influenza A, discovering variant strains, predicting and preventing and controlling the epidemic. Therefore, it is particularly urgent to establish a fast, accurate, simple and highly sensitive detection method.

Influenza B virus is one of the main pathogens of influenza, mainly through droplet and contact transmission, and the crowd is generally sensitive. Symptoms caused by influenza B virus are characterized by rapid onset, chills, and fever, with body temperature rising to a peak within a few hours to 24 hours, at 39-40° C. or even higher; accompanied by headache, body aches, fatigue, and loss of appetite; mild respiratory symptoms, dry throat, sore throat, dry cough, may have diarrhea; facial flushing, conjunctival hyperemia, pharyngeal hyperemia, and follicles on the soft palate. Influenza B viruses can be divided into different lineages according to the antigenic characteristics and the nucleic acid sequence of the hemagglutinin (HAI) gene. Most of the lineages of viruses have disappeared in natural selection, and have evolved into two lineages with large antigenic differences, called Yamagata lineage and Victoria lineage (referred to as Y lineage and V lineage).

The 2019 Novel coronavirus (2019-nCoV or SARS-CoV-2) is a non-segmented, single-stranded positive-sense RNA virus belonging to the subfamily Orthocorona mirinae, family Coronaviridae, and the Nidovirales order. According to serotype and genome characteristics, the subfamily Coronaviridae is divided into four genera. The virus is sensitive to heat and lipid solvents, such as 56° C. for 30 minutes, 75% ethanol, chlorine-containing disinfectant, peracetic acid, and chloroform can effectively inactivate the virus, but chlorhexidine cannot effectively inactivate the virus. The main clinical symptoms are fever, fatigue, and dry cough. Upper respiratory symptoms such as nasal congestion and runny nose are rare. About half of the patients developed dyspnea more than a week later, and severe cases rapidly progressed to acute respiratory distress syndrome, septic shock, metabolic acidosis that was difficult to correct, and coagulation dysfunction. It is worth noting that severe and critically ill patients may have moderate to low fever during the course of the disease, or even no obvious fever. Some patients have mild onset symptoms, may have no fever, and usually recover after 1 week. Most patients have a good prognosis, and a few patients are in critical condition and even died.

Influenza A virus, influenza B virus, and 2019-nCoV are all respiratory viruses. Influenza A virus and influenza B virus are the most common influenza pathogens. The initial symptoms of infected people are very similar to those of the 2019-nCoV infection, and both will show symptoms such as fever and cough. Therefore, it is difficult to make an accurate differential diagnosis of patients from clinical symptoms.

At present, common detection methods for influenza A virus, influenza B virus and 2019-nCoV nucleic acid include single pathogen detection technology based on fluorescent PCR technology, high-throughput sequencing method, constant temperature amplification, etc. Fluorescent PCR technology has high detection specificity and strong sensitivity, and the operation is relatively simple, but when multiple pathogens are detected at the same time, it is often necessary to carry out targeted detection in different tubes. Different pathogens may have certain differences in PCR amplification conditions, so they need to be checked one by one in clinical application, leading to a longer period of pathogen determination. Although high-throughput sequencing technology can detect multiple unknown sequences at the same time, there are problems such as long detection cycle, high cost, complicated operation, and difficult data interpretation. Although the constant temperature amplification technology has a short detection time, its detection equipment is not mature, and it is necessary to add enough new instruments to carry out supporting detection when clinical reagents are applied.

Therefore, there is an urgent need in this field to develop methods that can efficiently detect and identify clinically common respiratory viruses to meet clinical needs. In addition, it has been reported that the existing clinically used nucleic acid detection kits have the problem of low accuracy, so it is necessary to develop kit products with high clinical detection accuracy.

SUMMARY OF THE INVENTION

The purpose of the present invention is to provide a method and kit for multiple detection of respiratory virus nucleic acid.

In the first aspect of the present invention, it provides a primer pair set for multiplex detection of respiratory virus nucleic acid comprising:

a first primer pair group, wherein the first primer pair group comprises:

a forward primer as shown in SEQ ID NO.5 and a reverse primer as shown in SEQ ID NO.6.

In another preferred embodiment, the primer pair set further includes:

a second primer pair group, wherein the second primer pair group comprises:

a forward primer as shown in SEQ ID NO.7 and a reverse primer as shown in SEQ ID NO.8.

In another preferred embodiment, the primer pair set further includes:

a third primer pair group, wherein the third primer pair group comprises:

a forward primer as shown in SEQ ID NO.1 and a reverse primer as shown in SEQ ID NO.2.

In another preferred embodiment, the primer pair set further includes:

a fourth primer pair group, wherein the fourth primer pair group comprises:
a forward primer as shown in SEQ ID NO.3 and a reverse primer as shown in SEQ ID NO.4.

In another preferred embodiment, the primer pair set further includes:
a fifth primer pair group, wherein the fifth primer pair group comprises:
a forward primer as shown in SEQ ID NO.9 and a reverse primer as shown in SEQ ID NO.10.

A second aspect of the present invention provides a probe set for detecting respiratory virus nucleic acid, which includes:
one or more detection probes selected from the group consisting of SEQ ID NO.11, SEQ ID NO.12, SEQ ID NO.13, SEQ ID NO.14, SEQ ID NO.15.

In another preferred embodiment, the 5' end of each probe is labeled with a fluorescent reporter group; and/or, the 3' end of each probe is labeled with a fluorescence quenching group.

In another preferred embodiment, the fluorescent reporter groups labeled on the probes are different from each other.

In the third aspect of the present invention, it provides a kit for multiplex detection of respiratory virus nucleic acid, which comprises the primer pair set according to the first aspect of the present invention.

In another preferred embodiment, the kit further comprises the probe set according to the second aspect of the present invention.

In another preferred embodiment, the kit contains a first container, the first container contains a primer-probe mixture, and the primer-probe mixture contains multiple primers and multiple probes, wherein the primers contain polynucleotide sequences shown in SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 respectively; and the probes contain polynucleotide sequences shown in SEQ ID NO: 11, SEQ ID NO: 12, SEQ ID NO: 13, and SEQ ID NO: 14.

In another preferred embodiment, the first container further contains 5×RNA buffer and DEPC water.

In another preferred embodiment, the primer-probe mixture further contains primers with polynucleotide sequences shown in SEQ ID NO: 9 and SEQ ID NO: 10; and a probe with the polynucleotide sequence shown in SEQ ID NO: 15.

In another preferred embodiment, the fluorescent reporter groups labeled on the probes are different from each other.

In another preferred embodiment, the kit further comprises a second container, and the second container contains Hot-start Taq enzyme, Reverse transcriptase and dNTPs.

In another preferred embodiment, the kit further includes a third container, and the third container contains a positive control. Preferably, the positive control includes virus-like particles having Influenza A virus gene, Influenza B virus gene, 2019-nCoV ORF1ab gene, 2019-nCoV N gene and internal standard GAPDH gene.

In another preferred embodiment, the kit further includes a fourth container, and the fourth container contains a negative control. Preferably, the negative control is pure water.

In the fourth aspect of the present invention, it provides a method for multiplex detection of novel coronavirus nucleic acid comprising the following steps:
(1) providing a nucleic acid sample of a subject to be tested;
(2) preparing a PCR reaction system and perform fluorescent quantitative PCR detection:

wherein the PCR reaction system includes: the nucleic acid sample provided in step (1), the primer pair set according to the first aspect of the present invention, and the probe set according to the second aspect of the present invention.

In another preferred embodiment, the PCR reaction system includes the nucleic acid sample provided in step (1) and primer-probe mixture, and the primer-probe mixture contains multiple primers and multiple probes, wherein the primers contain polynucleotide sequences shown in SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 respectively; the probes contain polynucleotide sequences shown in SEQ ID NO: 11, SEQ ID NO: 12, SEQ ID NO: 13, and SEQ ID NO: 14.

In another preferred embodiment, the primer-probe mixture further contains primers with polynucleotide sequences shown in SEQ ID NO: 9 and SEQ ID NO: 10; and a probe with the polynucleotide sequence shown in SEQ ID NO: 15.

In another preferred embodiment, the fluorescent reporter groups labeled on the probes are different from each other.

In another preferred embodiment, the nucleic acid sample can be from a human nasopharyngeal swab, throat swab or sputum sample.

In another preferred embodiment, the method is a non-diagnostic detection method.

In a fifth aspect of the present invention, it provides a use of the primer pair set according to the first aspect of the present invention, and/or the probe set according to the second aspect of the present invention for preparing a PCR detection kit, the PCR detection kit is used to detect respiratory virus nucleic acid.

It should be understood that, within the scope of the present invention, the technical features specifically described above and below (such as the examples) can be combined with each other, thereby constituting a new or preferred technical solution which needs not be described one by one.

DETAILED DESCRIPTION OF INVENTION

Figure 1:
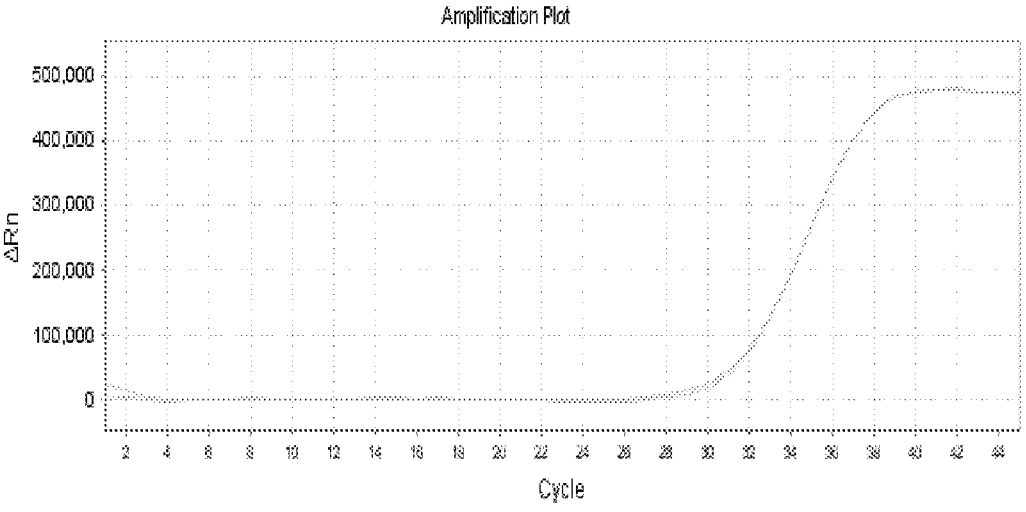
FIG. 1: Schematic diagram of the results of the negative control for the detection by the present invention.
Figure 2:
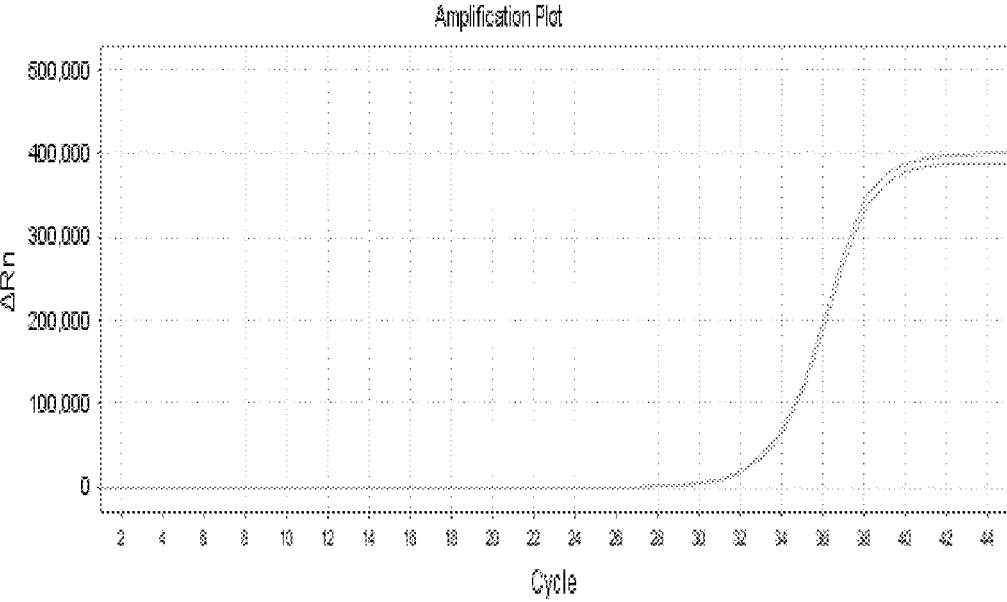
FIG. 2: Schematic diagram of the results of the positive control for the detection of Influenza A virus by the present invention.
Figure 3:
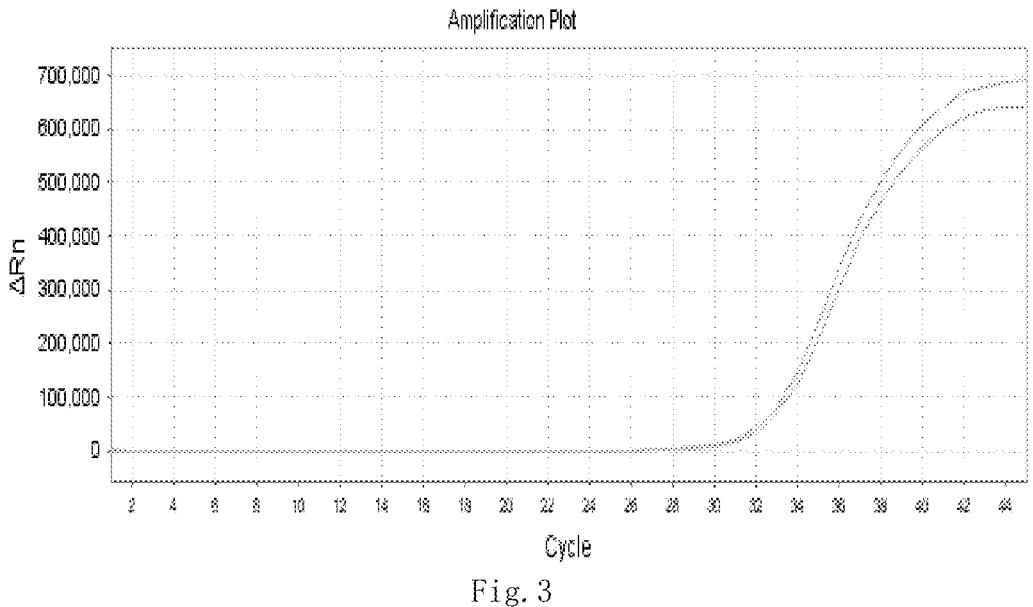
FIG. 3: Schematic diagram of the results of the positive control for the detection of Influenza B virus by the present invention.
Figure 4:
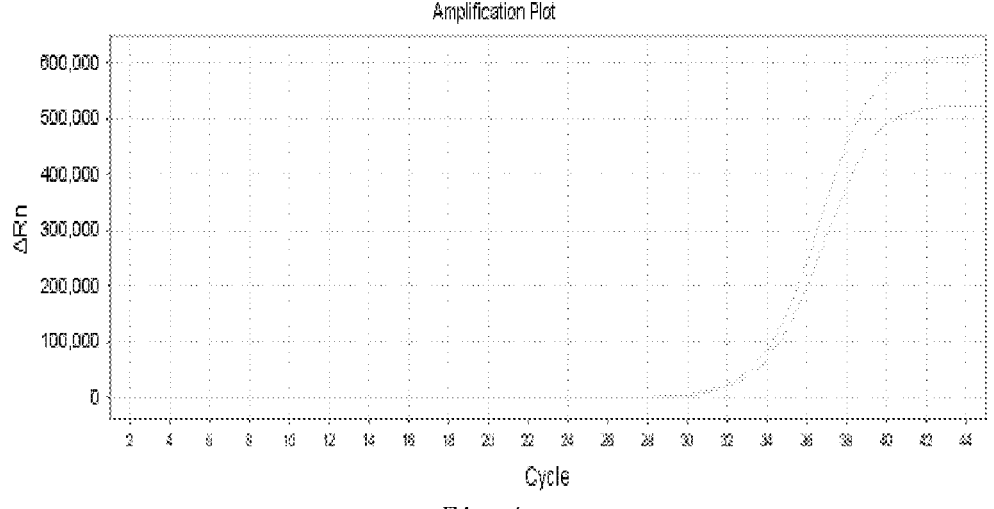
FIG. 4: Schematic diagram of the results of the positive control for the detection of the 2019-nCoV ORF1ab gene by the present invention.
Figure 5:
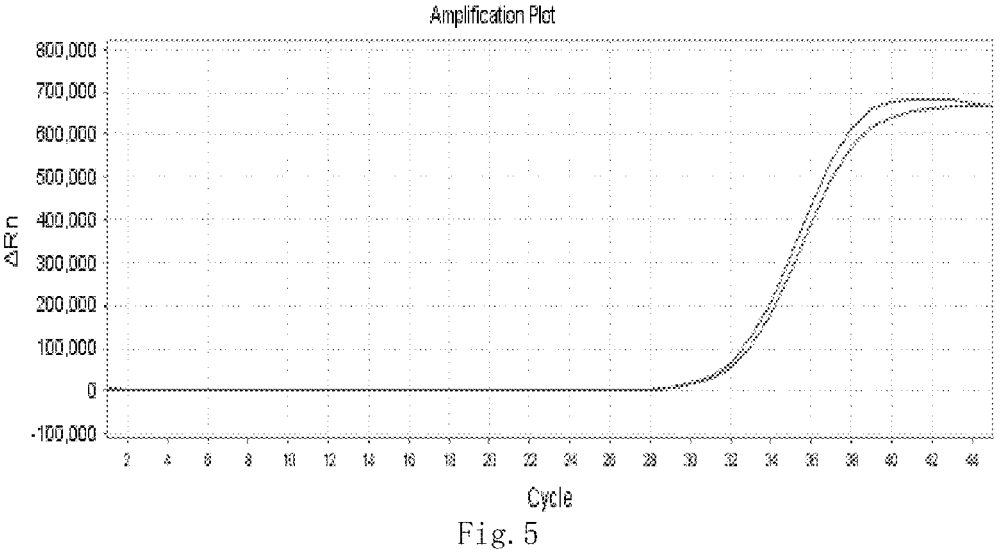
FIG. 5: Schematic diagram of the results of the positive control for the detection of the 2019-nCoV N gene by the present invention.
Figure 6:
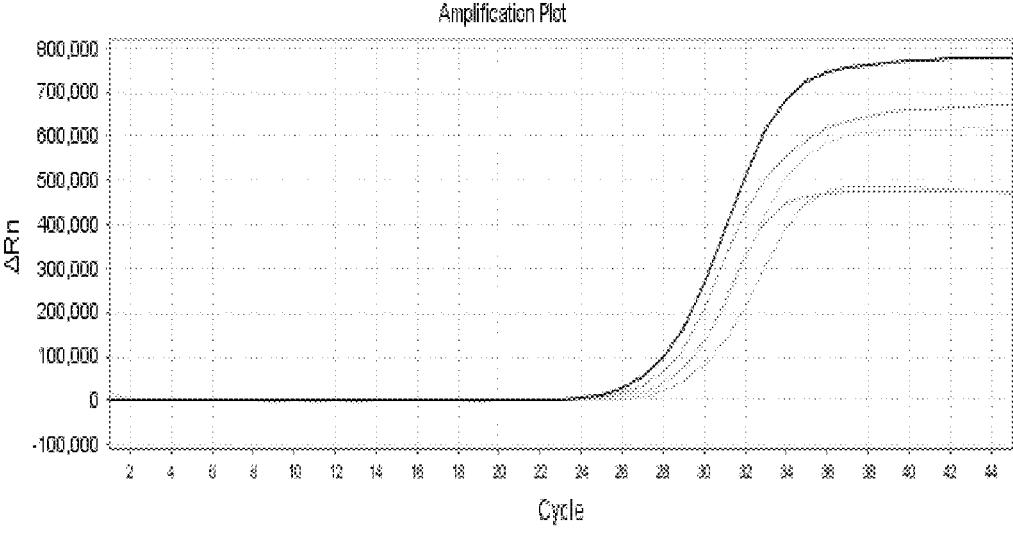
FIG. 6: Schematic diagram of the results of the present invention for detecting positive controls for Influenza A virus, Influenza B virus, and 2019-nCoV.

Through extensive and intensive research, the present inventor has obtained a kit and method for multiplex detection of the respiratory virus nucleic acid. Specifically, the present invention provides a method, primers, probes and kits based on a real-time fluorescent quantitative PCR technology platform, which can perform multiple detection of Influenza A virus (H1N1 (2019), H3N2, H5N1, H1N1, H7N9 and other), Influenza B virus (Yamagata, Victoria and other), 2019-nCoV (OFR1ab, N gene) and human internal standard gene GAPDH in nasopharyngeal swabs, throat swabs or sputum samples from patients with suspected influenza or Novel coronavirus pneumonia. It has the advantages of simple detection operation, absolute quantification, high sensitivity, strong specificity and good repeatability.

Fluorescent PCR technology is one of the most commonly used technologies in clinical pathogen detection. However, due to the strong signal interference between the fluorescent channels, the pathogen detection commonly used in clinical practice is mostly single-tube single-plex detection. Through a large number of screening and optimization tests, the present invention finally combines the detection of Influenza A virus, Influenza B virus and 2019-nCoV into one PCR reaction tube, and uses 5 different fluorescent channels to detect each pathogen. The test minimizes the interference between channels, and at the same time uses the human housekeeping gene as an internal standard to monitor the process of sample collection and extraction, effectively avoiding false negative results.

Multiplex PCR, also known as multiplex primer PCR or composite PCR, is a PCR reaction in which two or more pairs of primers are added to the same PCR reaction system to simultaneously amplify multiple nucleic acid fragments. The reaction principle, reaction reagents and operation process are the same as those of general PCR.

There are many factors that affect multiplex PCR reactions, such as:

(1) The reaction system is unbalanced. The imbalance of the reaction system leads to the rapid amplification of some dominant primers and their templates in the previous rounds of reactions, and a large number of amplification products are obtained, and these amplification products are also DNA polymerases good inhibitor. Therefore, with the large amount of amplification products, the polymerization ability of the polymerase is inhibited more and more strongly, so that the primers and their templates, which were at a disadvantage in the early stage, are even more difficult to react at this time, which eventually leads to a very small amount of amplification products, so much so that they cannot be detected.

(2) Primer specificity. If the primer has a stronger binding force to other non-target gene fragments in the system, the ability of the target gene to bind the primer will be competed, resulting in a decrease in amplification efficiency.

(3) The optimal annealing temperature is inconsistent. Multiple pairs of primers are placed in one system for amplification. Since the annealing temperature of the PCR reaction is the same, the optimal annealing temperature of each pair of primers is required to be close.

(4) Primer dimers, including the dimer between primers and the hairpin structure formed by the primer itself, and there is also a third-party DNA-mediated polymer. These dimers, like non-specific primers, interfere with the competition between the primer and the target binding site and affect the amplification efficiency.

Although several factors affecting amplification efficiency are mentioned above, many more factors are still unclear. So far, there is no effective method for unambiguously predicting amplification efficiency.

Multiplex fluorescent PCR technology can qualitatively detect multiple nucleic acid molecules in one PCR reaction tube. When detecting Influenza A virus, Influenza B virus and 2019-nCoV nucleic acid, it can be specifically amplified by combining different fluorescently labeled probes. The primers are used in a PCR reaction system to realize simultaneous detection of multiple pathogens under uniform PCR amplification conditions. The method has the advantages of high sensitivity, specific detection results of each fluorescence channel without signal crosstalk, stable detection results, simple and time-saving operation, etc.

It should be understood that the present invention is not limited to the specific methods and experimental conditions as described, due to such methods and conditions may vary. It should also be understood that the terminology used herein is for the purpose of describing specific embodiments only and is not intended to be limiting, and the scope of the present invention will be limited only by the appended claims.

Unless otherwise defined, all technical and scientific terms used herein have the same meaning as commonly understood by those of ordinary skill in the art to which this invention belongs. As used herein, when used in reference to specifically recited values, the term "about" means that the value may vary from the recited value by no more than 1%. For example, as used herein, the expression "about 100" includes all values between 99 and 101 and (e.g., 99.1, 99.2, 99.3, 99.4, etc.).

Although any methods and materials similar or equivalent to those described in the present invention can be used in the practice or testing of the present invention, the preferred methods and materials are exemplified herein.

The present invention provides a method, primers, probes and kits based on a platform of real-time fluorescent PCR for multiple detection of Influenza A viruses such as H1N1 (2019), H3N2, H5N1, H1N1, H7N9; Influenza B viruses such as Yamagata and Victoria; 2019-nCoV OFR1ab, N gene and human internal standard gene. It provides specific primers, probes and kit premixes for the detection of 2019-nCoV OFR1ab and N gene detection. It can be used to detect human nasopharyngeal swabs, throat swabs or sputum samples.

In a preferred embodiment, the primers include primers for influenza A viruses such as H1N1 (2019), H3N2, H5N1, H1N1, H7N9; influenza B viruses such as Yamagata and Victoria; 2019-nCoV OFR1ab, N gene and human internal standard gene GAPDH.

Among them, the nucleotide sequence of the universal upstream primer for Influenza A viruses such as H1N1 (2019), H3N2, H5N1, H1N1, H7N9 and other is shown in SEQ ID NO: 1, and the nucleotide sequence of the universal downstream primer for Influenza A virus such as H1N1 (2019), H3N2, H5N1, H1N1, H7N9 and other is shown in SEQ ID NO: 2.

The nucleotide sequence of the universal upstream primer for Influenza B viruses such as Yamagata and Victoria is shown in SEQ ID NO: 3, and the nucleotide sequence of the universal downstream primer for Influenza B viruses such as Yamagata and Victoria is shown in SEQ ID NO: 4.

The nucleotide sequence of the upstream primer for the 2019-nCoV OFR1ab gene is shown in SEQ ID NO: 5, and the nucleotide sequence of the downstream primer for the 2019-nCoV OFR1ab gene is shown in SEQ ID NO: 6.

The nucleotide sequence of the upstream primer for the 2019-nCoV N gene is shown in SEQ ID NO: 7, and the nucleotide sequence of the downstream primer for the 2019-nCoV N gene is shown in SEQ ID NO: 8.

The nucleotide sequence of the upstream primer for the internal standard GAPDH gene is shown in SEQ ID NO: 9, and the nucleotide sequence of the downstream primer for the internal standard GAPDH gene is shown in SEQ ID NO: 10.

The nucleotide sequence of the universal fluorescent probe for Influenza A viruses such as H1N1 (2019), H3N2, H5N1, H1N1, H7N9 and other is shown in SEQ ID NO: 11;

The nucleotide sequence of the universal fluorescent probe for Influenza B viruses such as Yamagata and Victoria is shown in SEQ ID NO: 12;

The sequence of the fluorescent probe for 2019-nCoV OFR1ab gene is shown in SEQ ID NO: 13;

The sequence of the fluorescent probe for 2019-nCoV N gene is shown in SEQ ID NO: 14;

The sequence of the fluorescent probe for the human housekeeping gene GAPDH is shown in SEQ ID NO:15;

Further, the SEQ ID NO: 11 nucleotide sequence is labeled with FAM at the 5' end and MGB at the 3' end; the SEQ ID NO: 12 nucleotide sequence is labeled with TexasRed at the 5' end and MGB at the 3' end; the SEQ ID NO: 13 nucleotide sequence is labeled with VIC at the 5' end and BHQ2 at the 3' end; the SEQ ID NO: 14 nucleotide sequence is labeled with TAMRA at the 5' end and BHQ2 at the 3' end; the SEQ ID NO: 15 nucleotide sequence is labeled with CY5 at the 5' end and MGB at the 3' end.

Preferably, the final concentration of the upstream primer SEQ ID NO: 1 and the downstream primer SEQ ID NO: 2 in the reaction system is 200 nmol/L; the final concentration of the upstream primer SEQ ID NO: 3, upstream primer SEQ ID NO: 9, downstream primer SEQ ID NO: 4 and downstream primer SEQ ID NO: 10 in the reaction system is 240 nmol/L; the final concentration of the upstream primer SEQ ID NO: 5, the upstream primer SEQ ID NO: 7, the downstream primer SEQ ID NO: 6 and the downstream primer SEQ ID NO: 8 in the reaction system is 1000 nmol/L; the final concentration of the probe SEQ ID NO: 11 in the reaction system is 40 nmol/L; the final concentration of the probe sequence SEQ ID NO: 12 in the reaction system is 120 nmol/L; the final concentration of the probe sequence SEQ ID NO: 13 in the reaction system is 200 nmol/L; the final concentration of the probe sequence SEQ ID NO: 14 in the reaction system is 240 nmol/L; the final concentration of the probe sequence SEQ ID NO: 15 in the reaction system is 160 nmol/L.

Detection primers and probes sequences for Influenza A viruses (H1N1 (2019), H3N2, H5N1, H1N1, H7N9 and other), Influenza B viruses (Yamagata, Victoria and other), 2019-nCoV (OFR1ab, N gene) and human internal standard gene GAPDH are as follows:

| Primer, Probe Sequence Number | Nucleotide Sequence (5'-3') |
|---|---|
| Influenza A virus universal upstream detection primer SEQ ID NO: 1 | AGACCAATCCTGTCACCTCTG |
| Influenza A virus universal downstream detection primer SEQ ID NO: 2 | CGTCTACGCTGCAGTCCTC |
| Influenza B virus universal upstream detection primer SEQ ID NO: 3 | GCGCTACTATACTGTCTCATGG |
| Influenza B virus universal downstream detection primer SEQ ID NO: 4 | TTGTTTCTCGCATAAAGCACA |
| 2019-nCoV OFR1ab upstream primer SEQ ID NO: 5 | CAAAGAATGCTATTAGAAAAGTGTG |
| 2019-nCoV OFR1ab downstream primer SEQ ID NO: 6 | CGACATTCATCATTATGCCTT |
| 2019-nCoV N upstream primer SEQ ID NO: 7 | ACCAGGAACTAATCAGACAAGGA |
| 2019-nCoV N downstream primer SEQ ID NO: 8 | GGTGTGACTTCCATGCCAAT |
| Human internal standard gene GAPDH upstream primer SEQ ID NO: 9 | AGATTTGGACCTGCGAGC |
| Human internal standard gene GAPDH downstream primer SEQ ID NO: 10 | ACTGAATAGCCAAGGTGAGC |
| General detection probe for influenza A virus SEQ ID NO: 11 | FAM-TTGTATTCACGCTCACCGTGC-MGB |
| General detection probe for influenza B virus SEQ ID NO: 12 | TexasRed-TCCTGGAAATTATTCAATGCAA GTA-MGB |

-continued

| Primer, Probe Sequence Number | Nucleotide Sequence (5'-3') |
|---|---|
| 2019-nCoV OFR1ab probe SEQ ID NO: 13 | VIC-AAATTATGGTGATAGTGCAACA-BHQ2 |
| 2019-nCoV N probe SEQ ID NO: 14 | TAMRA-CACAATTTGCCCCCAGCGCT-BHQ2 |
| Human internal standard gene GAPDH probe SEQ ID NO: 15 | CY5-TCCACAAGTCCGCGCAGAGC-MGB |

The specific primers and probes can accurately detect whether a human is infected with influenza A virus, influenza B virus or 2019-nCoV. At the same time, the 2019-nCoV ORF1ab and N genes were tested, and the test results were double confirmed. The human housekeeping gene GAPDH is used as the internal standard to monitor the quality of the nucleic acid, and when the quality of the sample is determined to be qualified, the suspected infection of the 2019-nCoV will be tested and confirmed.

The kit prepared by the above-mentioned specific primers and probes can detect influenza A virus, influenza B virus, 2019-nCoV ORF1ab and N gene in one PCR reaction tube at the same time based on the commonly used clinical fluorescent PCR platform, so as to diagnose patients in time and isolation treatment to provide a basis for diagnosis.

In a preferred embodiment of the present invention, the present invention also discloses 2019-nCoV nucleic acid detection kit used to detect a human nasopharyngeal swab, throat swab or sputum sample, including a primer-probe mixtures for preparing a PCR reaction, 5×RNA buffer, hot start Taq enzyme and reverse transcriptase, control sample and RNase-free water, wherein, the primer-probe mixture comprises the following components, as shown in Table 1,

TABLE 1

|  |  | Primer Probe Mixture |
|---|---|---|
| Serial number | Composition | The Main Ingredient in the Composition |
| 1 | Primer-probe mixture A for detection of influenza A virus, influenza B virus, 2019-nCoV ORF1ab gene, 2019-nCoV N gene and internal standard | Primers and probes for detecting 5 common influenza A viruses, 2 influenza B viruses, 2019-nCoV ORF1ab gene, 2019-nCoV N gene and human housekeeping gene GAPDH (SEQ ID NOs: 1-15) |

Wherein, the SEQ ID NO: 11 is labeled with a FAM fluorescent reporter group at the 5' end and a BHQ1 fluorescent quencher group at the 3' end; the SEQ ID NO: 12 is labeled with a TexasRed fluorescent reporter group at the 5' end and a MGB group at the 3' end; the SEQ ID NO: 13 is labeled with a VIC fluorescent reporter group at the 5' end and a BHQ1 fluorescent quencher group at the 3' end; the SEQ ID NO: 14 is labeled with a TAMRA fluorescent reporter group at the 5' end and a BHQ1 fluorescent quencher group at the 3' end; the SEQ ID NO: 15 is labeled with a CY5 fluorescent reporter group at the 5' end and a MGB group at the 3' end.

When the sample is detected, the general upstream and downstream primers and probes of influenza A virus combine with the amplified target fragment respectively, releasing the FAM fluorescent signal; the general upstream and downstream primers and probes of influenza B virus combine with the amplified target fragment respectively, releasing TexasRed fluorescent signal; 2019-nCoV ORF1ab gene amplification primers and probes respectively combine with the amplified target fragment, releasing VIC fluorescent signal; 2019-nCoV N gene amplification primers and probes respectively combine with the amplified target fragments, releasing TAMRA fluorescent signals; the internal standard gene amplification primers and probes, respectively combine with the amplified target fragment, releasing CY5 fluorescent signal. The internal control primers and probes are designed and synthesized based on the conserved fragments of human housekeeping genes, and are used for monitoring samples and experimental processes;

The 5×RNA buffer of the PCR reaction solution includes the following components, as shown in Table 2,

TABLE 2

|  | 5 × RNA buffer |  |
|---|---|---|
| Serial number | Composition | The Main Ingredient in the Composition |
| 1 | 5 × RNA buffer | (NH₄)₂SO₄, KCl, Tris-HCl, MgCl₂ |

The reference substance includes the following composition, as shown in Table 3,

TABLE 3

|  | Control samples |  |
|---|---|---|
| Serial number | Composition | The Main Ingredient in the Composition |
| 1 | Negative control | DEPC water |
| 2 | Positive control | Artificial virus-like particles |

The positive control is artificially prepared virus-like particles of influenza A virus, influenza B virus, 2019-nCoV (OFR1ab gene, N gene) and internal standard gene. And the negative control sample is DEPC water.

The applicable samples of the kit of the present invention are human nasopharyngeal swabs, throat swabs or sputum samples.

The standard that the kit of the present invention is used to determine the validity of the test is: a negative control group and a positive control group are set for each detection, when the test result of the positive control group is positive and the test result of the negative control group is negative, the experimental result is efficient.

The invention also discloses a method for qualitative detection of influenza A virus, influenza B virus and 2019-nCoV virus nucleic acid, the specific steps include:

1. Process the samples to be tested and extract nucleic acid samples. The samples can be human nasopharyngeal swabs, throat swabs or sputum samples. Preferably, the samples to be tested are human nasopharyngeal swabs or throat swabs.

2. Prepare a PCR reaction system. Mixing specific primers and probes, 5×RNA buffer, hot start Taq enzyme and reverse transcriptase, and adding 5 µL of extracted nucleic acid to prepare influenza A virus/influenza B virus/2019-nCoV Virus PCR reaction solution; and the composition of the reaction solution is shown in Table 4,

TABLE 4

| PCR reaction solution of influenza A virus, influenza B virus and 2019-nCoV | |
| --- | --- |
| Primer-probe mixture A for detection of influenza A virus, influenza B virus, 2019-nCoV ORF1ab gene, 2019-nCoV N gene and internal standard | 1 µL |
| Nucleic acid | 5 µL |
| 5 × RNA buffer | 5 µL |
| Hot start Taq enzyme + reverse transcriptase | 3 µL |
| DEPC water | 11 µL |

3. Put the PCR reaction tubes into the sample slot of the instrument, and record the order of placement.

4. Fluorescence channel selection:
1) Select the FAM channel to detect influenza A virus;
2) Select the VIC channel to detect the 2019-nCoV ORF1ab gene;
3) Select the TexasRed channel to detect influenza B virus;
4) Select the TAMRA channel to detect the 2019-nCoV N gene;
5) Select the CY5 channel to detect the internal standard gene;
6) Select the reference fluorescence (Passive Reference) as None.

5. Set the cycle conditions as shown in the table below, and set the volume of the reaction system to 25 µL.

| Step | Temperature (° C.) | Running time | Cycles | Data Collection |
| --- | --- | --- | --- | --- |
| 1 | 50 | 15 minutes | 1 | / |
| 2 | 95 | 15 minutes | 1 | / |
| 3 | 94 | 15 minutes | 45 | / |
| | 55 | 45 seconds | | √ |

6. After the setting is complete, save the file and run the program.

The PCR detection principle adopted in this application is as follows: apply real-time fluorescent PCR technology, design specific primers and probes in a PCR reaction tube to detect influenza A virus, influenza B virus or 2019-nCoV that may exist in human nasopharyngeal swabs, oropharyngeal swabs or sputum samples. Design specific primers and probes, use different fluorescent reporter groups to label influenza A virus, influenza B virus and 2019-nCoV respectively, and form nucleic acid amplification reagents together with hot start DNA polymerase, reverse transcriptase and other components, using a fluorescent PCR machine for PCR amplification, and detection the fluorescent signals. The extracted nucleic acid is added to the PCR reaction tube, and the instrument software system automatically draws a real-time amplification curve, and realizes qualitative detection of unknown samples according to the threshold cycle value (Ct value).

Compared with prior art, the beneficial effects of the present invention include:

The invention provides a method, primers, probes and kits for detecting human influenza A virus, influenza B virus and 2019-nCoV nucleic acid. Using the specific primers and probes provided by the present invention can rapidly, high sensitively and stably detect whether a suspected infected person is infected with influenza A virus, influenza B virus or 2019-nCoV. The minimum virus copy number that can be detected by the present invention is 200 copies/mL, and has relatively high sensitivity. The operation process is simple, and the qualitative detection of three pathogens can be completed in one reaction tube. Among them, the detected influenza A virus covers 5 common subtypes in China including H1N1 (2009), H1N1, H3N2, H5N1, H7N9, and the detected influenza B virus covers 2 subtypes including Yamagata and Victoria. The 2019-nCoV adopts double-target detection makes the detection results more reliable. At the same time, the human housekeeping gene is used as the internal standard to control the nucleic acid quality and sample collection, effectively eliminating the occurrence of false negative results. The present invention is suitable for detecting viral nucleic acid of suspected influenza or novel coronavirus pneumonia, confirming the diagnosis of patients, assisting and guiding clinicians to carry out treatment work, and is worthy of popularization and application.

In addition, the method of the present invention is also suitable for non-diagnostic purposes, for example, environmental samples can be tested to meet the needs of public health management, and can also be used for the development of new drugs for common respiratory viruses.

The present invention will be further described in detail below in conjunction with specific embodiments. It should be understood that these examples are only used to illustrate the present invention and not to limit the scope of the present invention. The experimental methods without detailed conditions in the following examples are generally in accordance with the conditions described in the conventional conditions such as Sambrook. J et al. "Guide to Molecular Cloning Laboratory" (translation by Huang Peitang et al., Beijing: Science Press, 2002), or as recommended by the manufacturer. Unless otherwise stated, percentages and parts are calculated by weight. Unless otherwise specified, the experimental materials and reagents used in the following examples can be obtained from commercially available channels.

Example 1 Detection Method and Kit

This embodiment provides methods, primers, probes and kits that can simultaneously detect influenza A virus, influenza B virus, 2019-nCoV and internal standard nucleic acid in one reaction tube, so that the sensitivity of the detection system can reach 200 copies/mL. The specific implementation steps are as follows:

Step 1. RNA Template Extraction of Samples to be Tested

Collect human nasopharyngeal swab samples, put the swab head into the tube containing the sampling solution, mark it to ensure that the label information is correct, and store it at 4° C. Within 12 hours, take 200 µL of liquid samples and the negative and positive controls in a kit for nucleic acid extraction. Nucleic acid extraction or purification kits (Magnetic Bead Method) produced by Sun Yat-Sen University Daan Gene Co., Ltd. can be used (Yuesuixiebei No. 20170583 and Yuesuixiebei No. 20150302); other commercial products can also be used. The extracted template nucleic acid can be used directly for subsequent experiments or stored at −80° C. for future use, avoiding repeated freezing and thawing.

Step 2, Preparation of PCR System

Preparation before PCR system preparation: Take out the primer-probe mixture A, 5×RNA buffer, hot-start Taq enzyme and reverse transcriptase in the kit, melt at room temperature, vortex and oscillate to mix well, and then centrifuge for 10 seconds to prepare the PCR system. The composition of the PCR system is shown in Table 6:

TABLE 6

| Influenza A virus/Influenza B virus/2019-nCoV PCR system | |
| --- | --- |
| Primer-probe mixture A for detection of influenza A virus, influenza B virus, 2019-nCoV ORF1ab gene, 2019-nCoV N gene and internal standard | 1 μL |
| Nucleic acid | 5 μL |
| 5 × RNA buffer | 5 μL |
| Hot start Taq enzyme + reverse transcriptase | 3 μL |
| DEPC water | 11 μL |

The nucleotide sequence information of the primer probe is as follows:

nucleotide sequence information of primers and probes for detecting influenza A virus/influenza B virus/2019-nCoV:

Step 3, Add Sample

Take 5 μL each of the sample nucleic acid template and the control sample prepared in step 1, and add the sample to the eight-tube tube of the PCR reaction system prepared in step 2, so that the total volume of the PCR reaction solution is L; tightly cover the tube cap of the eight-tube tube, mixed well, and centrifuged at high speed for 10 seconds, used to prepare micro-reactions; the control samples of the kit are shown in Table 7:

TABLE 7

| Control samples of the kit | | |
| --- | --- | --- |
| Serial number | Components | The Main Ingredient in the Composition |
| 1 | Negative control | DEPC water |
| 2 | Positive control | Artificial virus-like particles |

The positive control sample is a mixture of artificially prepared virus-like particle samples containing influenza A virus, influenza B virus, 2019-nCoV (ORF1ab gene, N gene) and internal standard GAPDH gene; the negative control sample is DEPC water.

Step 4, PCR Amplification

Put the PCR reaction tubes into the sample slot of the instrument, and record the order of placement. Select FAM

| Primers, Probes Sequence Number | Nucleotide Sequence (5'-3') |
| --- | --- |
| Influenza A virus universal upstream detection primer SEQ ID NO: 1 | AGACCAATCCTGTCACCTCTG |
| Influenza A virus universal downstream detection primer SEQ ID NO: 2 | CGTCTACGCTGCAGTCCTC |
| Influenza B virus universal upstream detection primer SEQ ID NO: 3 | GCGCTACTATACTGTCTCATGG |
| Influenza B virus universal downstream detection primer SEQ ID NO: 4 | TTGTTTCTCGCATAAAGCACA |
| 2019-nCoV OFR1ab upstream primer SEQ ID NO: 5 | CAAAGAATGCTATTAGAAAAGTGTG |
| 2019-nCoV OFR1ab downstream primer SEQ ID NO: 6 | CGACATTCATCATTATGCCTT |
| 2019-nCoV N upstream primer SEQ ID NO: 7 | ACCAGGAACTAATCAGACAAGGA |
| 2019-nCoV N downstream primer SEQ ID NO: 8 | GGTGTGACTTCCATGCCAAT |
| Human internal standard gene GAPDH upstream primer SEQ ID NO: 9 | AGATTTGGACCTGCGAGC |
| Human internal standard gene GAPDH downstream primer SEQ ID NO: 10 | ACTGAATAGCCAAGGTGAGC |
| General detection probe for influenza A virus SEQ ID NO: 11 | FAM-TTGTATTCACGCTCACCGTGC-MGB |
| General detection probe for influenza B virus SEQ ID NO: 12 | TexasRed-TCCTGGAAATTATTCAATGCAA GTA-MGB |
| 2019-nCoV OFR1ab probe SEQ ID NO: 13 | VIC-AAATTATGGTGATAGTGCAACA-BHQ2 |
| 2019-nCoV N probe SEQ ID NO: 14 | TAMRA-CACAATTTGCCCCCAGCGCT-BHQ2 |
| Human internal standard gene GAPDH type probe SEQ ID NO: 15 | CY5-TCCACAAGTCCGCGCAGAGC-MGB | channel to detect influenza A virus; select VIC channel to detect 2019 novel coronavirus ORF1ab gene; select Texas-Red channel to detect influenza B virus.

Select the TAMRA channel to detect the 2019 novel coronavirus N gene; select the CY5 channel to detect the internal standard gene; select the reference fluorescence (Passive Reference) as None, set the cycle conditions as shown in the table below, and set the reaction system volume to 25 μL; after the setting is complete, save the file, to run the program.

| Step | Temperature (° C.) | Running time | Cycle | Data Collection |
|------|--------------------|--------------|-------|-----------------|
| 1 | 50 | 15 minutes | 1 | / |
| 2 | 95 | 15 minutes | 1 | / |
| 3 | 94 | 15 minutes | 45 | / |
|   | 55 | 45 seconds |   | √ |

Step 5. Result Reading and Analysis

The results are automatically saved after the reaction, and the appropriate baseline and threshold are determined according to the amplification curve. The Start value of the Baseline is generally recommended to be between 3 and 15; the End value of the baseline is generally recommended to be between 5 and 20; the Threshold value is recommended to detect the highest fluorescence for each channel 1/20 of the value. After the baseline and threshold settings are completed, click Reanalyse to automatically obtain the Ct value of each channel, and judge the result according to the Ct value of each channel.

The composition, packaging and quantity (48 reactions/box) of the influenza A virus/influenza B virus/2019 novel coronavirus multiplex PCR detection kit provided in this example are shown in Table 8:

Example 2 Sensitivity Detection and Minimum Detection Rate Experiment

The no-template control sample is the nucleic acid containing the internal standard gene from the Caco2 cell line; the sensitivity reference product 1-3 is composed of influenza A virus-like particles, influenza B virus-like particles, and 2019-nCoV ORF1ab gene in different concentration gradients, 2019 novel coronavirus N gene and internal standard gene virus-like particle mixture sample composition, the concentrations of each mixture were 1000 copies/mL, 500 copies/mL, 200 copies/mL; the negative control was DEPC water;

Extract the nucleic acid of the no-template control, negative control, and sensitivity reference product, take 5 μL each, add the sample to the eight-tube tube of the PCR reaction system prepared in step 2, and do 20 replicates for each system of each sample, so that each tube of PCR reaction the total volume of the solution is L; tightly cap the eight-tube tube, mix well, and centrifuge at high speed for 10 seconds.

Put the PCR reaction tubes into the sample slot of the instrument, and record the order of placement. Select FAM channel to detect influenza A virus; select VIC channel to detect 2019 novel coronavirus ORF1ab gene; select Texas-Red channel to detect influenza B virus;

Select the TAMRA channel to detect the 2019 novel coronavirus N gene; select the CY5 channel to detect the internal standard gene; select the reference fluorescence (Passive Reference) as None, set the cycle conditions as shown in the table below, and set the reaction system volume to 25 μL; after the setting is complete, save the file, to run the program

TABLE 8

Components, packaging and quantity of the kit

| Serial Number | Components | Main Ingredient | Size (μL) | Quantity |
|---------------|-----------|-----------------|-----------|----------|
| 1 | Detection of influenza A virus, influenza B virus, 2019 novel coronavirus ORF1ab gene, 2019 novel coronavirus N gene PCR reaction solution A | The nucleotide sequences of primers and probes shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15; 5 × RNA buffer, DEPC water | 860 μL/tube | 1 |
| 2 | PCR reaction solution B | Hot Start Taq, Reverse transcriptase, dNTPS | 310 μL/tube | 1 |
| 3 | positive control | Artificially prepared virus-like particle sample mixture of influenza A virus, influenza B virus, 2019-nCoV ORF1ab gene, N gene and internal standard GAPDH gene | 200 μL/tube | 1 |
| 4 | negative control | DEPC water | 200 μL/tube | 1 |

| Step | Temperature (° C.) | Running time | Cycle | Data Collection |
|---|---|---|---|---|
| 1 | 50 | 15 minutes | 1 | / |
| 2 | 95 | 15 minutes | 1 | / |
| 3 | 94 | 15 minutes | 45 | / |
|  | 55 | 45 seconds |  | √ |

Step 5. Result Reading and Analysis

The results are automatically saved after the reaction, and the appropriate baseline and threshold are determined according to the amplification curve. The Start value of the Baseline is generally recommended to be between 3 and 15; the End value of the baseline is generally recommended to be between 5 and 20; the threshold value is recommended to be 1/20 of the highest fluorescence value detected by each channel. After the baseline and threshold settings are completed, click Reanalyse to automatically obtain the Ct value of each channel, and judge the result according to the Ct value of each channel.

Use the PCR system to measure the sample detection range of the present invention, and the actual measured results are as shown in Table 9,

TABLE 9

Minimum detection limit test results

| | Minimum Detection Limit Test Results | | | | | |
|---|---|---|---|---|---|---|
| | 1000 copies/mL | | 500 copies/mL | | 200 copies/mL | |
| Type | Positive Responses/ Total Responses | Compliance rate (%) | Positive Responses/ Total Responses | Compliance rate (%) | Positive Responses/ Total Responses | Compliance rate (%) |
| Influenza A virus | 20/20 | 100% | 20/20 | 100% | 20/20 | 100% |
| Influenza B virus | 20/20 | 100% | 20/20 | 100% | 20/20 | 100% |
| 2019-nCoV ORF1ab | 20/20 | 100% | 20/20 | 100% | 20/20 | 100% |
| 2019-nCoV N | 20/20 | 100% | 20/20 | 100% | 20/20 | 100% |

The sensitivity detection result of this kit is consistent with the theoretical value, indicating that the primers and probes have good specificity, and the sensitivity detection is good; when detecting 200 copies/mL reference product, the PCR system can stably detect as positive. Therefore, the present invention can detect samples of 200 copies/mL.

Example 3 Accuracy Test

Preparation of reference products for accuracy: Influenza A virus cultures containing H1N1 (2009) subtypes, H1N1 subtypes, H3N2 subtypes, H5N1 subtypes, H7N9 subtypes; Influenza virus cultures containing Yamagata, Victoria subtype; 2019-nCoV ORF1ab gene virus-like particles, 2019-nCoV N gene virus-like particles and internal standard gene virus-like particles were respectively serially diluted to a concentration of 5000 copies/mL of accuracy reference products P1-P10;

Extract the accuracy reference substance, negative control and positive control nucleic acid; take 5 μL of the sample and add it to the eight-tube tube of the PCR reaction system prepared in step 2, and repeat each 3 times, so that the total volume of the PCR reaction solution is 25 μL. Tighten the cap of the eight-tube tube, mix well, and centrifuge at high speed for 10 seconds.

Put the PCR reaction tubes into the sample slot of the instrument, and record the order of placement. Select FAM channel to detect influenza A virus; select VIC channel to detect 2019-nCoV ORF1ab gene; select TexasRed channel to detect influenza B virus.

Select the TAMRA channel to detect the 2019-nCoV N gene; select the CY5 channel to detect the internal standard gene; select the reference fluorescence (Passive Reference) as None, set the cycle conditions as shown in the table below, and set the reaction system volume to 25 μL; after the setting is complete, save the file, run the program.

| Step | Temperature (° C.) | Running time | Cycle | Data Collection |
|---|---|---|---|---|
| 1 | 50 | 15 minutes | 1 | / |
| 2 | 95 | 15 minutes | 1 | / |
| 3 | 94 | 15 minutes | 45 | / |
|  | 55 | 45 seconds |  | √ |

Step 5. Result Reading and Analysis

The results are automatically saved after the reaction, and the appropriate baseline and threshold are determined according to the amplification curve. The Start value of the Baseline is generally recommended to be between 3 and 15; the End value of the baseline is generally recommended to be between 5 and 20; the Threshold value is recommended to be 1/20 of the highest fluorescence value detected by each channel. After the baseline and threshold settings are completed, click Reanalyse to automatically obtain the Ct value of each channel, and judge the result according to the Ct value of each channel.

The sample detection range of the present invention is measured with a PCR system, and the actual measured results are as shown in Table 10,

TABLE 10 accuracy test results

| Category | Concentration (Average) | Actual Qualitative Results | Theoretical Qualitative Guideline |
|---|---|---|---|
| H1N1(2009) | $1 \times 10^5$ copies/mL | positive | positive |
| H1N1 | $1 \times 10^5$ copies/mL | positive | positive |

TABLE 10-continued

| | | | |
|---|---|---|---|
| | | accuracy test results | |
| Category | Concentration (Average) | Actual Qualitative Results | Theoretical Qualitative Guideline |
| H3N2 | $1 \times 10^5$ copies/mL | positive | positive |
| H5N1 | $1 \times 10^5$ copies/mL | positive | positive |
| H7N9 | $1 \times 10^5$ copies/mL | positive | positive |
| Yamagata | $1 \times 10^5$ copies/mL | positive | positive |
| Victoria | $1 \times 10^5$ copies/mL | positive | positive |
| ORF1ab | $1 \times 10^5$ copies/mL | positive | positive |
| N | $1 \times 10^5$ copies/mL | positive | positive |

According to the results described in the above table, the positive rate of the detection results of the accuracy of each quality control product is 100%, which meets the theoretical requirements.

Example 4 Clinical Application Experiment

Collect 100 nasopharyngeal swab samples, negative controls and positive controls from patients with suspected influenza or novel coronavirus pneumonia, dip the swab heads into tubes containing sampling fluid, mark the samples and ensure that the label information is correct, and store them at 4° C. Nucleic acid extraction or purification kits (Magnetic Bead Method) produced by Sun Yat-Sen University Daan Gene Co., Ltd. can be used, Yuesuixiebei No. 20170583 and Yuesuixiebei No. 20150302; other commercial products can also be used. The extracted template nucleic acid can be used directly for subsequent experiments or stored at −80° C. for future use, avoiding repeated freezing and thawing.

Take 5 µL of each nucleic acid, add the sample to the eight-tubes of the PCR reaction system prepared in step 2, so that the total volume of each tube of PCR reaction solution is 25 µL; tightly cap the eight-tube tubes, mix well, and centrifuge at high speed for 10 Second;

Put the PCR reaction tubes into the sample slot of the instrument, and record the order of placement. Select FAM channel to detect influenza A virus; select VIC channel to detect 2019-nCoV ORF1ab gene; select TexasRed channel to detect influenza B virus.

Select the TAMRA channel to detect 2019-nCoV N gene; select the CY5 channel to detect the internal standard gene; select the reference fluorescence (Passive Reference) as None, set the cycle conditions as shown in the table below, and set the reaction system volume to 25 µL; after the setting is complete, save the file, to run the program.

| Step | Temperature (° C.) | Running time | Cycle | Data Collection |
|---|---|---|---|---|
| 1 | 50 | 15 minutes | 1 | / |
| 2 | 95 | 15 minutes | 1 | / |
| 3 | 94 | 15 minutes | 45 | / |
| | 55 | 45 seconds | | √ |

Step 5. Result Reading and Analysis

The results are automatically saved after the reaction, and the appropriate baseline and threshold are determined according to the amplification curve. The Start value of the Baseline is generally recommended to be between 3 and 15; the End value of the baseline is generally recommended to be between 5 and 20; the Threshold value is recommended to be $1/20$ of the highest fluorescence value detected by each channel. After the baseline and threshold settings are completed, click Reanalyse to automatically obtain the Ct value of each channel, and judge the result according to the Ct value of each channel.

Use the PCR system to measure the sample detection range of the present invention, and the actual measured results are as shown in Table 11.

TABLE 11

| | | | | | | |
|---|---|---|---|---|---|---|
| | Test results of clinical samples | | | | | |
| Clinical Sample No. | Test Results The present Kit | | | Control Kit (Singleplex Fluorescent PCR for Each Pathogen) | | |
| | Influenza A virus | Influenza B virus | 2019 Novel Coronavirus | Influenza A virus | Influenza B virus | 2019 Novel Coronavirus |
| 1 | + | − | − | + | − | − |
| 2 | − | − | − | − | − | − |
| 3 | − | − | − | − | − | − |
| 4 | − | − | − | − | − | − |
| 5 | − | − | − | − | − | − |
| 6 | − | − | − | − | − | − |
| 7 | − | − | + | − | − | + |
| 8 | − | − | − | − | − | − |
| 9 | − | − | − | − | − | − |
| 10 | − | + | − | − | + | − |
| 11 | + | − | − | + | − | − |
| 12 | − | − | − | − | − | − |
| 13 | − | − | − | − | − | − |
| 14 | − | − | − | − | − | − |
| 15 | − | − | − | − | − | − |
| 16 | − | − | − | − | − | − |
| 17 | − | − | + | − | − | + |
| 18 | − | − | − | − | − | − |
| 19 | − | − | − | − | − | − |
| 20 | − | − | − | − | − | − |
| 21 | − | − | − | − | − | − |

TABLE 11-continued

| | Test Results The present Kit | | | Control Kit (Singleplex Fluorescent PCR for Each Pathogen) | | |
|---|---|---|---|---|---|---|
| Clinical Sample No. | Influenza A virus | Influenza B virus | 2019 Novel Coronavirus | Influenza A virus | Influenza B virus | 2019 Novel Coronavirus |
| 22 | – | – | – | – | – | – |
| 23 | – | – | – | – | – | – |
| 24 | – | – | – | – | – | – |
| 25 | – | – | – | – | – | – |
| 26 | – | – | – | – | – | – |
| 27 | – | – | – | – | – | – |
| 28 | – | – | – | – | – | – |
| 29 | – | – | – | – | – | – |
| 30 | – | – | – | – | – | – |
| 31 | – | – | – | – | – | – |
| 32 | – | – | – | – | – | – |
| 33 | – | – | + | – | – | + |
| 34 | + | – | – | + | – | – |
| 35 | – | – | – | – | – | – |
| 36 | – | – | – | – | – | – |
| 37 | – | – | – | – | – | – |
| 38 | – | – | – | – | – | – |
| 39 | – | – | – | – | – | – |
| 40 | – | – | + | – | – | + |
| 41 | – | – | – | – | – | – |
| 42 | – | – | – | – | – | – |
| 43 | – | – | – | – | – | – |
| 44 | – | – | – | – | – | – |
| 45 | – | – | – | – | – | – |
| 46 | – | – | – | – | – | – |
| 47 | – | – | – | – | – | – |
| 48 | – | – | – | – | – | – |
| 49 | – | – | + | – | – | + |
| 50 | – | – | – | – | – | – |
| 51 | – | – | – | – | – | – |
| 52 | + | – | – | + | – | – |
| 53 | – | – | – | – | – | – |
| 54 | – | – | – | – | – | – |
| 55 | – | – | – | – | – | – |
| 56 | – | + | – | – | + | – |
| 57 | – | + | – | – | + | – |
| 58 | – | – | – | – | – | – |
| 59 | – | – | – | – | – | – |
| 60 | – | – | – | – | – | – |
| 61 | – | – | – | – | – | – |
| 62 | – | – | – | – | – | – |
| 63 | – | – | – | – | – | – |
| 64 | – | – | – | – | – | – |
| 65 | – | – | – | – | – | – |
| 66 | – | – | – | – | – | – |
| 67 | – | – | + | – | – | + |
| 68 | – | – | – | – | – | – |
| 69 | – | – | – | – | – | – |
| 70 | – | – | – | – | – | – |
| 71 | – | – | – | – | – | – |
| 72 | – | – | – | – | – | – |
| 73 | – | – | – | – | – | – |
| 74 | – | – | – | – | – | – |
| 75 | – | – | – | – | – | – |
| 76 | – | – | – | – | – | – |
| 77 | – | – | – | – | – | – |
| 78 | – | – | – | – | – | – |
| 79 | – | – | – | – | – | – |
| 80 | – | – | – | – | – | – |
| 81 | + | – | – | + | – | – |
| 82 | – | – | + | – | – | + |
| 83 | – | – | – | – | – | – |
| 84 | – | – | – | – | – | – |
| 85 | – | – | – | – | – | – |
| 86 | – | – | – | – | – | – |
| 87 | – | – | – | – | – | – |
| 88 | – | – | – | – | – | – |
| 89 | – | – | – | – | – | – |
| 90 | – | – | – | – | – | – |
| 91 | – | – | – | – | – | – |
| 92 | – | – | – | – | – | – |

TABLE 11-continued

Test results of clinical samples

| Clinical Sample No. | Test Results The present Kit | | | Control Kit (Singleplex Fluorescent PCR for Each Pathogen) | | |
|---|---|---|---|---|---|---|
| | Influenza A virus | Influenza B virus | 2019 Novel Coronavirus | Influenza A virus | Influenza B virus | 2019 Novel Coronavirus |
| 93 | – | – | – | – | – | – |
| 94 | – | + | – | – | + | – |
| 95 | – | – | – | – | – | – |
| 96 | – | – | – | – | – | – |
| 97 | – | – | – | – | – | – |
| 98 | – | – | – | – | – | – |
| 99 | – | – | – | – | – | – |
| 100 | – | + | – | – | + | – |
| Accuracy | | | 100% | | | |
| Specificity | | | 100% | | | |

The test results showed that out of 100 samples, 7 samples were positive for 2019-nCoV, 5 were positive for influenza A virus, 5 were positive for influenza B virus, and the rest were negative. The consistency of the detected results with the corresponding pathogen single-plex fluorescent PCR results was 100%.

Comparative Example 1

During the research process, the inventor screened dozens of sets of PCR primers and probes for the target nucleic acid sequences of influenza A virus, influenza B virus, and novel coronavirus 2019-nCoV. After a large number of tests, the combination of primers and probes that can meet the needs of clinical detection with sensitivity and specificity and can perform multiple detection is finally obtained.

For example, for the novel coronavirus 2019-nCoV ORF1ab gene, some typical primer sequences designed by the inventors are as follows:

```
Comparative primer pair 1:
Upstream primers:
                        (SEQ ID NO. 16)
5'CGGGTGTTGCTATGCCTAATCT 3'

Downstream primers:
                        (SEQ ID NO. 17)
5'TTGCGACATTCATCATTATGCC 3'

Comparative primer pair 2:
Upstream primers:
                        (SEQ ID NO. 18)
5' CCCAAAATTACAATCTAGTCAAGCGT 3'

Downstream primers:
                        (SEQ ID NO. 19)
5' TGACACAGTTGAGTATATTTTGCGAC 3'

Comparative primer pair 3:
Upstream primers:
                        (SEQ ID NO. 20)
5' GGCCATGTAGAAACATTTTACCCAAA 3'

Downstream primers:
                        (SEQ ID NO. 21)
5' TTGAGTATATTTTGCGACATTCATCA 3'
```

The specific detection steps, detection conditions, and probe sequences are the same as those in the above examples, and the fluorescent PCR detection test is carried out.

Figure 7:
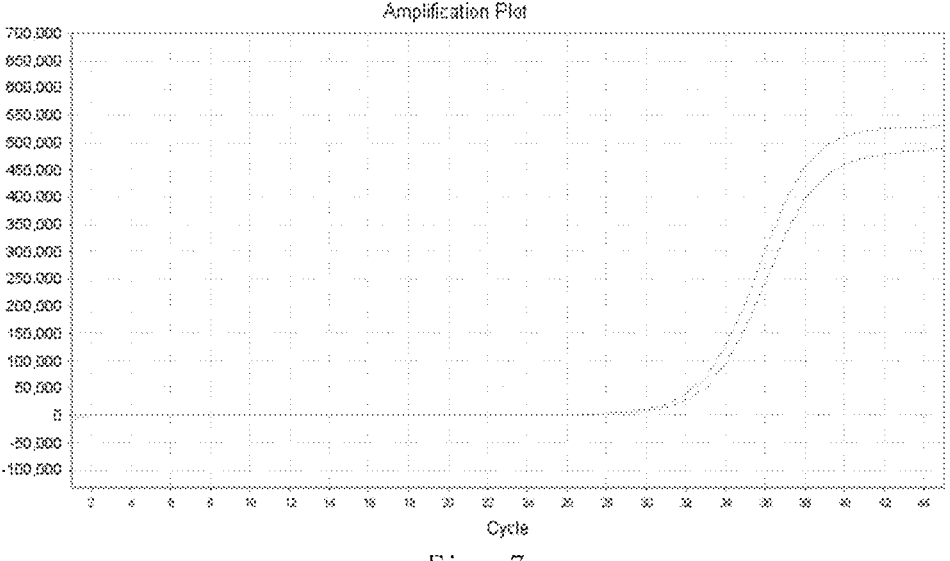
FIG. 7: Schematic diagram of the detection results of the specificity (non-specific amplification of Influenza A samples) of the 2019-nCoV ORF1ab gene Comparative primer pair 1.
Figure 8:
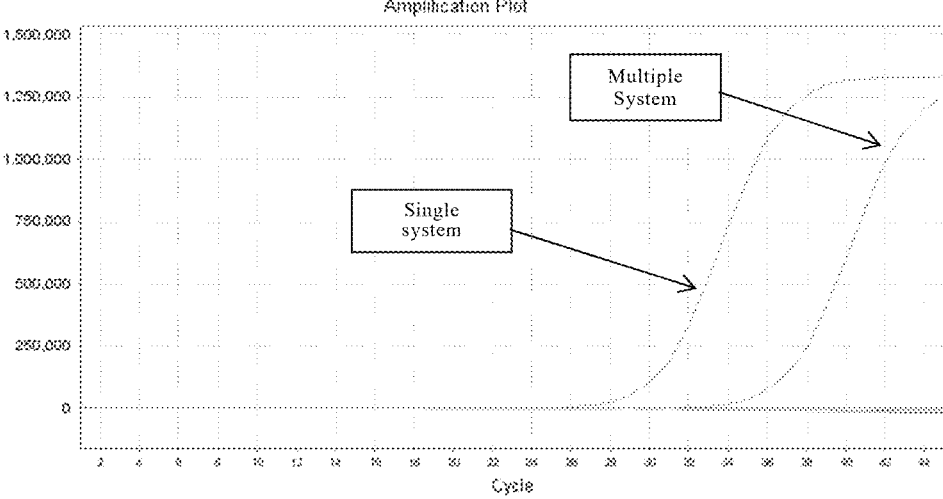
FIG. 8: Schematic diagram of the detection results of the 2019-nCoV ORF1ab gene Comparative primer pair 2.
Figure 9:
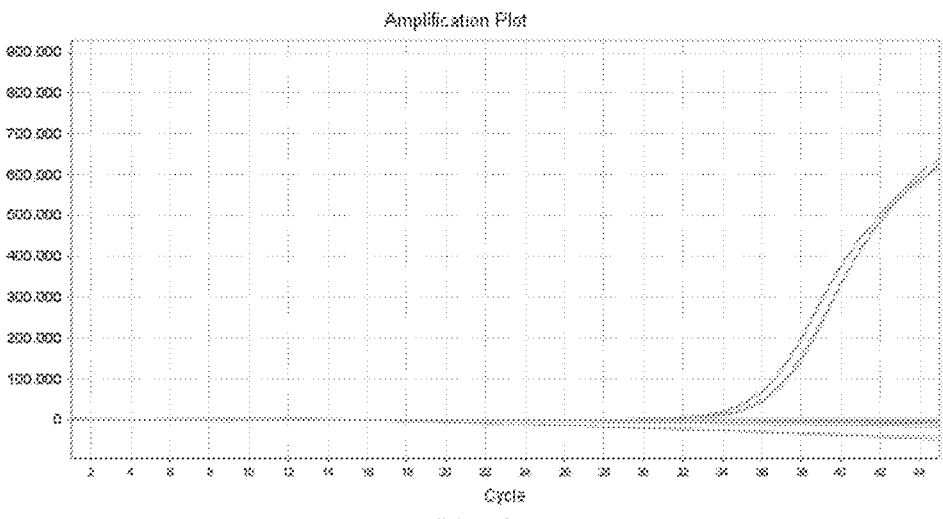
FIG. 9: Schematic diagram of the sensitivity detection results of the 2019-nCoV ORF1ab gene Comparative primer pair 3.

The detection result using the Comparative primer pair 1 is shown in FIG. 7, and the detection result shows that the specificity of the primer pair is poor. The detection results using the Comparative primer pair 2 show that the primer pair has better specificity and sensitivity to the ORF1ab gene target nucleic acid in a single detection system, but the low-concentration nucleic acid amplification of the ORF1ab gene target is significantly inhibited in the multiple detection system. The detection results of single and multiple systems are shown in FIG. 8. It shows that the Comparative primer pair 2 cannot be applied in the multiplex detection system. The detection results using the Comparative primer pair 3 shows that the primer pair has better specificity and sensitivity to the ORF1ab gene target nucleic acid in a single detection system and a multiple detection system, and the sensitivity can reach 200 copies/mL. The detection results are shown in FIG. 9.

At present, the positive detection of 2019 novel coronavirus (2019-nCoV) nucleic acid by real-time fluorescent PCR is the gold standard for the diagnosis of novel coronavirus pneumonia. However, the accuracy and reproducibility of the nucleic acid test of the existing kits are still found to be improved clinically, and cases of positive tests only after several nucleic acid tests are often reported.

Under the condition of ensuring specificity and sensitivity, the inventors screened out 8 groups of multiple nucleic acid detection systems. The nucleic acid of 7 nasopharyngeal swab samples positive for 2019-nCoV were used for testing. For the specific method, refer to Example 4. The results showed that the accuracy of clinical sample detection was less than 90% (less than 6/7) for six groups of multiplex nucleic acid detection systems. Among them, only the multiple nucleic acid detection system using the Comparative primer pair 3 and the multiple nucleic acid detection system of the present invention achieved 100% accuracy of clinical samples detection. Using these two multiple nucleic acid detection systems, clinical samples were tested 10 times, and the results showed that the multiple nucleic acid detection system containing the Comparative primer pair 3 failed to detect the ORF1ab target gene twice, and failed to detect the N target gene once, while the multiple nucleic acid detection system of the present invention detected the target gene in all 10 times, indicating that the multiple nucleic acid detection system of the present invention has stronger anti-interference ability and excellent clinical reliability.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

What is claimed:

1. A kit for multiplex detection of respiratory virus nucleic acid comprising a primer pair set and a probe set, the primer pair set comprising:
    a first primer pair group,
        wherein the first primer pair group comprises a forward primer as shown in SEQ ID NO: 5 and a reverse primer as shown in SEQ ID NO: 6;
    a second primer pair group,
        wherein the second primer pair group comprises a forward primer as shown in SEQ ID NO: 7 and a reverse primer as shown in SEQ ID NO: 8;
    a third primer pair group,
        wherein the third primer pair group comprises a forward primer as shown in SEQ ID NO: 1 and a reverse primer as shown in SEQ ID NO: 2;
    a fourth primer pair group,
        wherein the fourth primer pair group comprises a forward primer as shown in SEQ ID NO: 3; and a reverse primer as shown in SEQ ID NO: 4; and
    a fifth primer pair group,
        wherein the fifth primer pair group comprises a forward primer as shown in SEQ ID NO: 9 and a reverse primer as shown in SEQ ID NO: 10, and
    the probe set comprising probes respectively having polynucleotide sequences shown in SEQ ID NO: 11, SEQ ID NO: 12, SEQ ID NO: 13, SEQ ID NO: 14, and SEQ ID NO: 15,
        wherein the SEQ ID NO: 11 nucleotide sequence is labeled with FAM at a 5' end and MGB at a 3' end, the SEQ ID NO: 12 nucleotide sequence is labeled with TexasRed at a 5' end and MGB at a 3' end, the SEQ ID NO: 13 nucleotide sequence is labeled with VIC at a 5' end and BHQ2 at a 3' end, the SEQ ID NO: 14 nucleotide sequence is labeled with TAMRA at a 5' end and BHQ2 at a 3' end, and the SEQ ID NO: 15 nucleotide sequence is labeled with CY5 at a 5' end and MGB at a 3' end.

2. The kit of claim 1, further comprising a first container, which comprises a primer-probe mixture, wherein the primer-probe mixture contains-comprises multiple primers and multiple probes,
    the primers respectively having the polynucleotide sequences shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, and
    the probes respectively having the polynucleotide sequences shown in SEQ ID NO: 11, SEQ ID NO: 12, SEQ ID NO: 13, SEQ ID NO: 14, and SEQ ID NO: 15.

3. The kit of claim 2, wherein the kit further comprises a second container comprising a hot-start enzyme, a reverse transcriptase, and dNTPs.

4. The kit of claim 3, wherein the kit further comprises a third container comprising a positive control.

5. A multiplex PCR method for detecting influenza A virus (IAV), influenza B virus (IBV), and SARS-COV-2 nucleic acids comprising:

extracting a nucleic acid template from a subject test sample;
    mixing the nucleic acid template with a PCR reaction system comprising the following components:
    an IAV primer pair consisting of an upstream primer consisting of SEQ ID NO: 1 and a downstream primer consisting of SEQ ID NO: 2;
    an IBV primer pair consisting of an upstream primer consisting of SEQ ID NO: 3 and a downstream primer consisting of SEQ ID NO: 4;
    a 2019-nCOV OFR 1ab upstream primer pair consisting of SEQ ID NO: 5 and a downstream primer consisting of SEQ ID NO: 6;
    a 2019-nCOV N upstream primer pair consisting of SEQ ID NO: 7 and a downstream primer SEQ ID NO: 8;
    an internal standard GAPDH primer pair consisting of an upstream primer consisting of SEQ ID NO: 9 and a downstream primer consisting of SEQ ID NO: 10; and
    labeled detection probes consisting of SEQ ID NOs: 11-15, wherein the SEQ ID NO: 11 is labeled with FAM at a 5' end and MGB at a 3' end; the SEQ ID NO: 12 is labeled with TexasRed at a 5' end and MGB at a 3' end; the SEQ ID NO: 13 is labeled with VIC at a 5' end and BHQ2 at a 3' end; the SEQ ID NO: 14 is labeled with TAMRA at a 5' end and BHQ2 at a 3' end; and the SEQ ID NO: 15 is labeled with CY5 at a 5' end and MGB at a 3' end;
    performing real-time fluorescent PCR; and
    detecting amplified DNA using different fluorescent channel curves.

6. The method of claim 5, wherein a reaction of the real-time fluorescent PCR comprises:
    a first stage of holding at 50° C. for 15 min followed by holding at 95° C. for 15 min for 1 cycle; and
    a second stage of holding at 94° C. for 15 s followed by holding at 55° C. for 45 s for 45 cycles.

7. The kit of claim 4, wherein the kit further comprises a fourth container comprising a negative control.

*    *    *    *    *